United States Patent [19]

Abou-Gharbia

[11] Patent Number: 4,812,567

[45] Date of Patent: Mar. 14, 1989

[54] POLYCYCLIC SPIROIMIDES WITH PSYCHOTROPIC ACTIVITY

[75] Inventor: Magid A. Abou-Gharbia, Wilmington, Del.

[73] Assignee: American Home Products Corporation, New York, N.Y.

[21] Appl. No.: 942,897

[22] Filed: Dec. 17, 1986

Related U.S. Application Data

[63] Continuation-in-part of Ser. No. 787,950, Oct. 16, 1985, abandoned.

[51] Int. Cl.[4] .................. C07D 401/14; C07D 403/14; C07D 491/107
[52] U.S. Cl. .................................. 544/230; 540/543; 544/238; 544/295; 544/357; 546/15; 546/16; 546/17; 548/408; 548/410; 548/411; 549/233
[58] Field of Search .................. 540/543; 544/230; 546/15, 16, 17, 18; 548/407, 408, 409, 410, 411

[56] References Cited

U.S. PATENT DOCUMENTS

| | | | |
|---|---|---|---|
| 3,200,118 | 8/1965 | Grogan et al. | 548/408 |
| 3,717,634 | 2/1973 | Wu et al. | 544/230 |
| 4,305,944 | 12/1981 | Temple, Jr. et al. | 544/230 |
| 4,543,355 | 9/1985 | Ishizumi et al. | 544/230 |
| 4,613,601 | 9/1986 | Regnier et al. | 514/252 |
| 4,619,930 | 10/1986 | New et al. | 514/253 |
| 4,675,403 | 6/1987 | Abou-Gharbia et al. | 544/230 |
| 4,701,456 | 10/1987 | Dewald et al. | 514/253 |

FOREIGN PATENT DOCUMENTS 983493  2/1976  Canada .

OTHER PUBLICATIONS

Science Union et al. Cie-Societe Francaise de Recherche Medicale, Chemical Abstracts vol. 85, 63049y (1976).

Primary Examiner—Donald G. Daus
Assistant Examiner—E. Bernhardt
Attorney, Agent, or Firm—George Tarnowski

[57] ABSTRACT

There are disclosed compounds of the formula

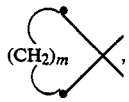

wherein
$R^1$ and $R^2$ taken together represent

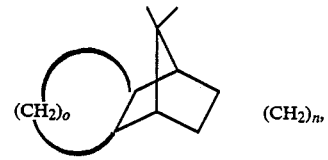

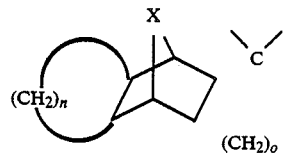

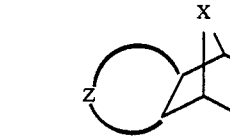

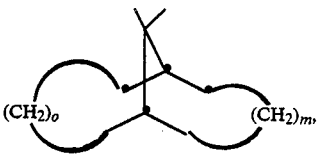

or

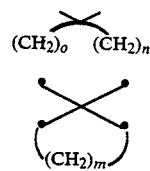

with the proviso that in

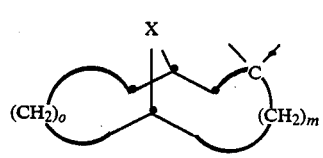

when X is lower alkylene or O, m is other than 1; and when $R^1$ and $R^2$ taken together represent
(Abstract continued on next page.)

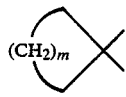

$R^3$ is other than unsubstituted or substituted 2-pyridinyl or 2-pyrimidinyl;

$R^3$ is unsubstituted or substituted 2-pyridinyl, 2-pyrimidinyl, 2-pyrazinyl or 3-pyridazinyl, where the substituents are selected from the group lower alkyl, lower alkoxy, halo, cyano and nitro;

Z is $-(CH_2)_n-$ or vinylene;
X is lower alkylene, vinylene or O;
m is 1–4;
n is 1–3;
o is 1–5;
p is 0–1;

and the pharmaceutically acceptable salts thereof and their use as antipsychotic/anxiolytic agents having a low liability for extrapyramidal side effects.

4 Claims, No Drawings

POLYCYCLIC SPIROIMIDES WITH PSYCHOTROPIC ACTIVITY

This application is a continuation-in-part of U.S. Ser. No. 787,950, filed Oct. 16, 1985, now abandoned.

This invention relates to novel compounds having antipsychotic activity and being characterized by the general formula

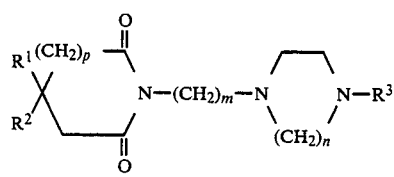

wherein $R^1$ and $R^2$ taken together represent

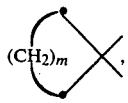

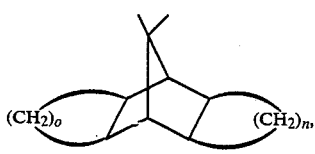

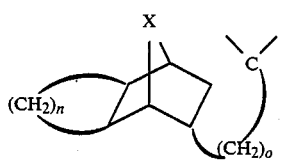

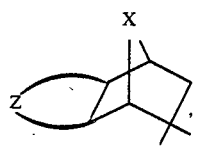

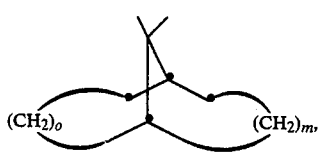

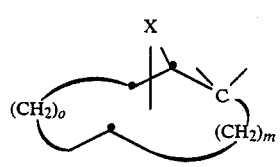

or

-continued

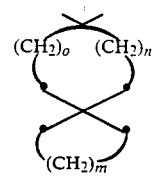

with the proviso that in

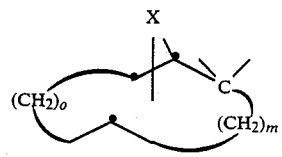

when X is lower alkylene or O, m is other than 1; and when $R^1$ and $R^2$ taken together represent

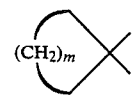

$R^3$ is other than unsubstituted or substituted 2-pyridinyl or 2-pyrimidinyl;

$R^3$ is unsubstituted or substituted 2-pyridinyl, 2-pyrimidinyl, 2-pyrazinyl or 3-pyridazinyl, where the substituents are selected from the group lower alkyl, lower alkoxy, halo, cyano and nitro;

Z is —$(CH_2)_n$— or vinylene;

X is lower alkylene, vinylene or O;

m is 1–4;

n is 1–3;

o is 1–5;

p is 0–1;

and the pharmaceutically acceptable salts thereof.

The term "lower alkyl" refers to moieties having 1–6 carbon atoms in the carbon chain. The term "alkoxy" refers to moieties having 1–6 carbon atoms. The term "lower alkylene" refers to saturated moieties having 1–4 carbon atoms in the carbon claim. The term "halo" refers to fluoro, chloro and bromo.

The compounds of the invention can form pharmacologically acceptable salts from pharmacologically acceptable organic and inorganic acids such as hydrochloric, hydrobromic, sulfonic, sulfuric, phosphoric, nitric, maleic, fumaric, benzoic, ascorbic, pamoic, succinic, methanesulfonic, acetic, propionic, tartaric, citric, lactic, malic, mandelic, cinnamic, palmitic, itaconic and benzenesulfonic.

The compounds of the invention may be prepared by a variety of synthetic routes using conventional methods.

Compounds of the invention can be prepared according to the following scheme illustrating the instance in which $R^1$ and $R^2$ represent the moiety

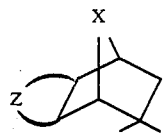

can be prepared from the corresponding fused bicyclospiro imide according to the following reaction scheme:

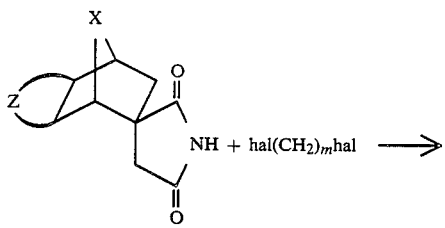

NH + hal(CH$_2$)$_m$hal ⟶

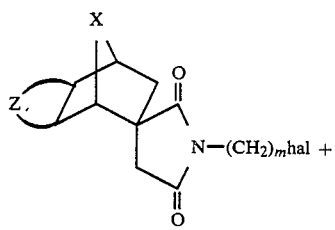

N—(CH$_2$)$_m$hal +

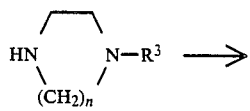

⟶

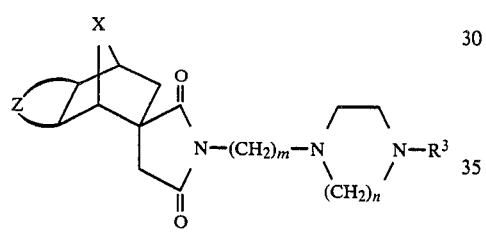

wherein X, Z, R$^3$, m, n and hal are as defined hereinbefore.

The bicyclospiro imides as used in the previous reaction scheme can be prepared according to standard synthetic reaction sequences such as those disclosed by Abou-Gharbia et al., *J. Pharm. Sci.*, 67, 953 (1978) and Rice et al., *J. Med. Chem.*, 17, 882 (1974). The general steps involved in such syntheses are as follows:

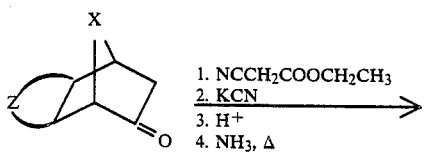

1. NCCH$_2$COOCH$_2$CH$_3$
2. KCN
3. H$^+$
4. NH$_3$, Δ

⟶

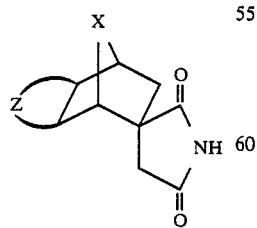

In order to obtain the various rings structures defined by R$^1$ and R$^2$, the aforementioned reaction sequence is carried out using appropriate starting ketones. Thus, the structure

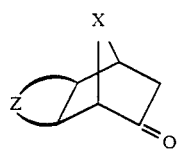

can be obtained by a Diels-Alder addition, as for example

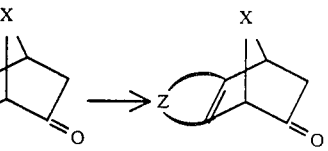

where the starting olefins are commercially available. Structures of the type

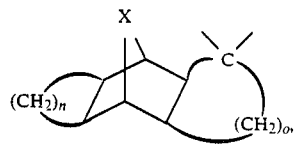

can be prepared by the folowing reaction sequence, exemplified for the structure

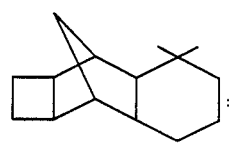

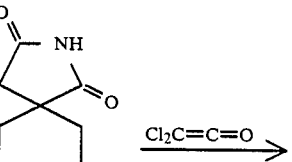

+  —Diels-Alder→ 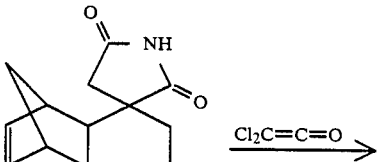

The latter cycloadduct ketone is then used to prepare the spiro-linked pyrrolidinedione as discussed supra. which, in turn, is reacted according to the method of Ghosez et al., *Tetrahedron*, 27, 615 (1971) and Krepski and Hassner, *J. Org. Chem.*, 43, 2879 (1978) to yield the desired intermediate

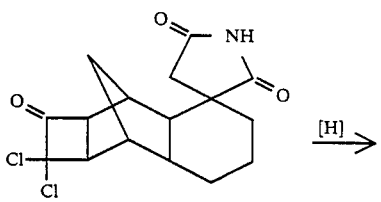

Cl$_2$C=C=O ⟶

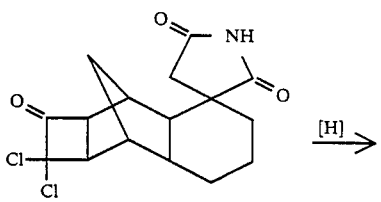

[H] ⟶

-continued

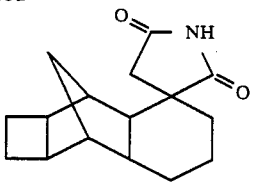

Starting compounds defined by the structure

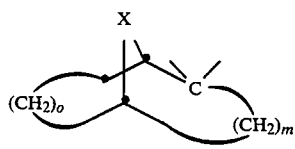

as for example

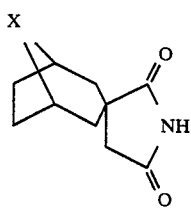

can be prepared from bicyclo[3.2.1]octan-3-one by the previously mentioned methods. The bicyclo[3.2.1]octan-3-one can be prepared from commercially available bicyclo[3.2.1]heptene by the method of Moore et al., *J. Org. Chem.*, 28, 2200 (1963). Starting compounds of the structure

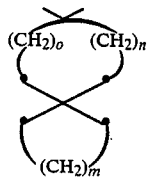

can be prepared by the method of Rice et al., *J. Med. Chem.*, 15, 548 (1972) starting with readily available 1,1-bis(bromoalkyl)cycloalkanes.

Of course, other methods of preparation, which will occur to those skilled in the art, may also be employed to prepare the compounds of the invention.

The compounds of the invention may exist either in the form of the free base or the pharmacologically acceptable salts. Methods for converting one such form to another will be obvious to one skilled in the chemical arts.

The compounds of the invention display a pharmacological profile like that of the compound buspirone (8-[4-[4-(2-pyrimidinyl)-1-piperazinyl]butyl]-8-azaspiro-[4.5]decane-7,9-dione). The latter compound has demonstrated preclinical activity in antipsychotic paradigms and has also displayed a unique clinical anxioselective profile, whereby its efficacy in the treatment of anxiety neuroses is comparable to the benzodiazepine diazepam but without the benzodiazepine-related side effects. The clinically effective anxiolytic doses of the benzodiazepines produce such undesirable side effects as ataxia, muscle relaxation and sedation. Additionally, most chronically used antipsychotic drugs, cause extrapyramidal side effects, such as pseudoparkinsonism, tardive dyskinesia and the like. Ideally, treatment of psychoses and anxiety should be free of any undesirable side effects. The compounds of the invention, in a manner similar to buspirone, display preclinical antipsychotic activity without or with minimal side effects. Moreover, based on their buspirone-like profile, the compounds of the invention can be considered of clinical value in treating anxiety neuroses.

When employed as anxiolytics/antipsychotics, the effective dosage of the substances active for such treatment will vary according to the particular compound being employed, the severity and nature of condition being treated. Therapy should be initiated at lower doses (in mg/kg/day), the dosage thereafter being increased, if necessary, to produce the desired effect. In general, the compounds of the invention are most desirably administered at a concentration that will generally afford effective results without causing any harmful or deleterious effects.

When the compounds of the invention are employed as anxiolytics/antipsychotic agents, they can be formulated into oral dosage forms such as tablets, capsules and the like. The compounds can be administered alone or by combining them with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter and the like. Diluents, flavoring agents, solubilizers, lubricants, suspending agents, binders, tablet-disintegrating agents and the like may be employed. The compounds may be encapsulated with or without other carriers. In all cases, the proportion of active ingredients in said compositions both solid and liquid will be at least to impart the desired activity thereto on oral administration. The compounds may also be injected parenterally in which case they are used in the form of a sterile solution containing other solutes, for example, enough saline or glucose to make the solution isotonic.

The antipsychotic activity of the compounds of the invention and their substantial lack of extrapyramidal side effects may be demonstrated by standard pharmacological procedures, which are described more fully in the examples given hereafter.

The following examples show the preparation and pharmacological testing of compounds within the invention.

EXAMPLE 1

1'-[4-[4-(2-Pyrimidinyl)-1-piperazinyl]butyl]spiro[bicyclo[3.2.1]octane-2,3'-pyrrolidine]-2',5'-dione, dihydrochloride, hemihydrate A mixture of bicyclo[3.2.1]octane-2-exo-2-endomethylenedicarboxylic anhydride 2 g (0.01 mol), 1-(4-aminobutyl)-4-(2-pyrimidinyl)piperazine 2.4 g (0.01 mol) and 50 ml of pyridine are refluxed overnight. The solvent is removed under reduced pressure and the remaining oil is purified by HPLC using ethyl acetate as an eluent. The title compound is converted to the hydrochloride salt by dissolving in ethanol and adding 10 ml ethanol saturated with hydrogen chloride; m.p. 233°–236° C.

Analysis for: $C_{23}H_{33}N_5O_2 \cdot 2HCl \cdot 1\frac{1}{2}H_2O$; Calculated: C, 55.98; H, 7.30; N, 14.19; Found: C, 56.21; H, 7.17; N, 14.08.

EXAMPLE 2

Octahydro-1'-[4-[4-(2-Pyrimidinyl)-1-piperazinyl]-butyl]spiro[4,7-methano-5H-indene-5,3'-pyrrolidine]-2',5'-dione, dihydrochloride The title compound is prepared following the procedure of Example 1 using tricyclo[5.2.1.0]decane-2-exo-2-endomethylenedicarboxylic anhydride instead of bicyclo[3.2.1]octane-2-exo-2-endomethylene dicarboxylic anhydride and is converted to the dihydrochloride salt; m.p. 228°–230° C.

Analysis for: $C_{24}H_{35}N_5O_2.2HCl$; Calculated: C, 57.82; H, 7.48; N, 14.05; Found: C, 57.99; H, 7.21; N, 13.52.

EXAMPLE 3

1'-[4-[4-(2-Pyrimidinyl)-1-piperazinyl]butyl]spiro[bicyclo[3.3.1]nonane-9-3'-pyrrolidine]-2',5'-dione, dihydrochloride, sesquihydrate The title compound is prepared following the procedure of Example 1, using bicyclo[3.3.1]nonane-9-exo-9-endomethylenedicarboxylic anhydride instead of bicyclo[3.2.1]octane-2-exo-2-endomethylenedicarboxylic anhydride and is converted to the dihydrochloride salt; m.p. 272°–273° C.

Analysis for: $C_{24}H_{35}N_5O_2.1\frac{1}{2}H_2O$; Calculated: C, 54.85; H, 7.61; N, 13.33; Found: C, 54.47; H, 7.10; N, 13.27.

EXAMPLE 4

8-[4-[4-(6-Chloro-2-pyrazinyl)-1-piperazinyl]butyl]-8-azaspiro[4,5]decane-7,9-dione dihydrochloride, hydrate A mixture of 3,3-tetramethyleneglutarimide, sodium hydride, 1-bromo-4-chlorobutane and dimethylformamide is stirred at room temperature for 48 hours.

The solvent is evaporated under reduced pressure and the residue is extracted with methylene chloride (3×200 mL). The methylene chloride extracts are collected, washed with water and dried (anhydrous $Na_2SO_4$). Evaporation of the methylene chloride under reduced pressure affords 8-(4-chlorobutyl)-8-azaspiro[4,5]decane-7,9-dione.

The title compound is prepared by dissolving 8-(4-chlorobutyl)-8-azaspiro[4,5]decane-7,9-dione in dimethylformamide and to that solution 1-(6-chloro-2-pyrazinyl)piperazine hydrochloride and triethylamine are added. Stirring is continued for 48 hours. The solvent is removed under reduced pressure and the residue is partitioned between water and methylene chloride. The methylene chloride extracts are combined, dried over anhydrous $Na_2SO_4$, filtered and evaporated under reduced pressure to give crude base. Preparative HPLC (silica gel; ethylacetate:methylene chloride) gives, following evaporation of the appropriate fractions ($R_f 0.5$), the title compound which is converted to the dihydrochloride salt; mp 138°–140° C.

Analysis for: $C_{11}H_{30}ClN_5O_2.2HCl.H_2O$; Calculated: C, 49.36; H, 6.70; N, 13.71; Found: C, 48.90; H, 6.57; N, 13.78.

EXAMPLE 5

8-[4-[4-(3-Chloro-2-pyrazinyl)-1-piperazinyl]butyl]-8-azaspiro[4,5]decane-7,9-dione dihydrochloride, hemihydrate The title compound is prepared following procedure of Example 4 using 1-(3-chloro-2-pyrazinyl)piperazine hydrochloride instead of 1-(6-chloro-2-pyrazinyl)piperazine hydrochloride and is converted to the hydrochloride salt; mp 178°–180° C.

Analysis for: $C_{21}H_{30}ClN_5O_2.HCl.\frac{1}{2}H_2O$; Calculated: C, 54.19; H, 6.88; N, 15.05. Found: C, 54.07; H, 6.92; N, 15.54.

EXAMPLE 6

8-[4-[4-(6-Chloro-3-pyridazinyl)-1-piperazinyl]-8-azaspiro[4,5]decane-7,9-dione dihydrochloride The title compound is prepared following procedure of Example 4 using 1-(6-chloro-3-pyridazinyl)piperazine instead of 1-(6-chloro-2-pyrazinyl)piperazine hydrochloride and is converted to the dihydrochloride salt; mp 268°–270° C.

Analysis for: $C_{21}H_{30}ClN_5O_2.2HCl$; Calculated: C, 51.17; H, 6.54; N, 14.21; Found: C, 51.05; H, 6.54; N, 14.02.

EXAMPLE 7

The compounds of the invention are tested in an assay to determine their ability to antagonise apomorphine-induced stereotyped behavior. The assay measures the in vivo dopamine reception blocking activity of the compounds and provides a means for gauging whether the compounds tested may potentially exhibit extrapyramidal side effects.

The assay is carried out as follows:

20–25 gm male CF-1 mice (Charles River) are used. The mice are tested one week before the experiment for a positive stereotyped response to 10 mg/kg s.c. apomorphine. Test compounds, suspended or solubilized in 0.25% Tween 80® in water, are administered at several dose levels to male mice (6/dose level). A control group, run simultaneously with drug groups, receives equal volumes of solvent. Thirty minutes later (i.p. administration) or 60 minutes later (p.o. administration), drug-treated and control mice are challenged with 10 mg/kg apormorphine s.c. Five minutes after the injection, the rearing-head-bobbing-licking syndrome induced by apomorphine is recorded as present or absent for each animal. Readings are repeated every 5 minutes during a 30 minute test session.

The number of positive or negative 5-minute intervals during which apomorphine-induced stereotyped behavior is present or absent is measured. $ED_{50}$ values (with 95% confidence intervals) are calculated for inhibition of apomorphine-induced stereotyped behavior, by a simple linear regression analysis with inverse prediction.

| STANDARD COMPOUNDS: | $ED_{50}$ and 95% confidence interval, mg/kg intraperitoneal |
|---|---|
| Haloperidol | 1.37 (0.88–2.34) |
| Chloropromazine | 8.48 (4.79–16.38) |
| Clozapine | 30.06 (19.42–48.21) |

The compounds of the invention, when tested in this assay are inactive, evidencing a low potential for exhibiting extrapyramidal side effects, such as pseudo parkinsonism, tardive dyskinesia and the like.

EXAMPLE 8

A test designed to determine the potential antipsychotic activity of the compounds of this invention is the conditioned avoidance (shelf-jump response) test.

This test is carried out as follows:

Male CD rats (Charles River) maintained at approximately 400-450 gm body weight are used. Previously trained rats are placed in plexiglass experimental chambers divided into two sections; a main chamber (10½"×6¾"×11⅞" high) and an elevated chamber or shelf (5⅞"×6⅞"×5¾"). A moveable wall, controlled by a motor, determines whether the rat has access to the shelf at any time during the experiment. The experimental chamber also contains a house light and sonalert. A steel grid floor in the main chamber is wired for presentation of electric shock. Each trial consists of a fifteen-second warning tone (conditioned stimulus), continuing for an additional fifteen seconds accompanied by electric shock, (unconditioned stimulus). A response (jumping onto the exposed shelf of the upper chamber) occurring during the initial fifteen-second warning tone is considered an avoidance response, while a response occurring during shock delivery is considered an escape response. Trials are presented on a fixed interval schedule of one minute. The session consists of thirty-six trials. Animals are run twice weekly with control sessions always preceding a drug run, and with at least one day intervening. Compounds are administered i.p. or p.o. at appropriate pre-treatment times to a minimum of five rats at each dose level over a range of doses.

The following experimental parameters are recorded by computer: (1) the number of avoidance responses, (2) the number of escape responses, and (3) the number of trials in which no response occurred. These data are used to calculate the percent difference from control values previously determined and are presented for visual comparison via a line graph.

Response counts are summed over all subjects at a given dose. The number of trials in which rats fail to exhibit an avoidance response (Avoidance Block, AB) is determined at each dose. This number is expressed as a percentage of the total trials. Control performance is arbitrarily assigned a value of 100% for avoidance and the dose calculated to produce a 50% block in avoidance responding (AB$_{50}$) is obtained from a dose-effect regression line fitted by the method of least squares. Potential antipsychotic compounds suppress avoidance responding and increase escape responding.

| STANDARD COMPOUNDS: | AB$_{50}$ (mg/kg i.p.) |
|---|---|
| Haloperidol | 0.19 |
| Chlorpromazine | 3.69 |
| Clozapine | 6.94 |
| Buspirone | 9.94 |

The results for compounds of this invention in this test are presented in Table 2.

TABLE 2

| Compound of Example No. | Active at (mg/kg) |
|---|---|
| 1 | 40 (i.p.)* |
| 2 | 40 (i.p.) |
| 4 | 40 (orally administered) |
| 5 | 40 (i.p.) |
| 6 | 40 (i.p.) |

*(i.p.) = intraperitoneally administered drug.

The results show that compounds of the invention are active intraperitoneally in this test.

What is claimed is:

1. A compound having the formula wherein
R$^1$ and R$^2$ taken together represent or R$^3$ is unsubstituted or monosubstituted 2-pyridinyl, 2-pyrimidinyl, 2-pyrazinyl or 3-pyridazinyl, where the substituents are selected from the group lower alkyl, lower alkoxy, halo, cyano and nitro;
Z is —(CH$_2$)$_n$— or vinylene;
X is lower alkylene, vinylene or O;
m is 1-4;
n is 1-3;
o is 1-5;
p is 0-1;
and the pharmaceutically acceptable salts thereof.

2. The compound having the name 1'-[4-[4-(2-pyrimidinyl)-1-piperazinyl]butyl]spiro[bicyclo[3.2.1]octane-2,3'-pyrrolidine]-2',5'-dione.

3. The compound having the name octahydro-1'-[4-[4-(2-pyrimidinyl)-1-piperazinyl]butyl]spiro[4,7-methano-5H-indene-5,3'-pyrrolidine]-2',5'-dione.

4. The compound having the name 1'-[4-[4-(2-pyrimidinyl)-1-piperazinyl]butyl]spiro[bicyclo[3.3.1]nonane-9,3'-pyrrolidine]-2',5'-dione.

* * * * *